(12) United States Patent
Henderson

(10) Patent No.: US 9,176,100 B2
(45) Date of Patent: Nov. 3, 2015

(54) FOREIGN BODY DETECTING

(75) Inventor: Jim Henderson, Fife (GB)

(73) Assignee: NCR Corporation, Duluth, GA (US)

( * ) Notice: Subject to any disclaimer, the term of this patent is extended or adjusted under 35 U.S.C. 154(b) by 988 days.

(21) Appl. No.: 13/330,025

(22) Filed: Dec. 19, 2011

(65) Prior Publication Data

US 2013/0152690 A1 Jun. 20, 2013

(51) Int. Cl.
*G01N 29/46* (2006.01)
*G01N 29/34* (2006.01)

(52) U.S. Cl.
CPC .............. *G01N 29/46* (2013.01); *G01N 29/343* (2013.01)

(58) Field of Classification Search
CPC .............................. G01N 29/46; G01N 29/343
USPC ..................................... 73/579, 648, 659, 602
See application file for complete search history.

(56) References Cited

U.S. PATENT DOCUMENTS

| | | | |
|---|---|---|---|
| 4,461,178 A * | 7/1984 | Chamuel ......................... | 73/599 |
| 5,932,806 A * | 8/1999 | Rose et al. ...................... | 73/599 |
| 2002/0005070 A1* | 1/2002 | Matuseski et al. .............. | 73/597 |
| 2002/0129654 A1* | 9/2002 | Hongerholt ..................... | 73/596 |

* cited by examiner

*Primary Examiner* — Laura Martin
*Assistant Examiner* — Rose M Miller
(74) *Attorney, Agent, or Firm* — Joseph P. Mehrle

(57) ABSTRACT

A self-service terminal has a fascia 1. A transmitter 18 sends a chirped ultrasonic pulse across a region R of the fascia. The pulse interacts with the region R and the region R responds by emitting an output. A receiver 20 receives the output and produces an electrical signal corresponding to the output. A frequency analysing module 24 transforms the electrical signal into a frequency response.

15 Claims, 2 Drawing Sheets

FOREIGN BODY DETECTING

FIELD OF THE INVENTION

The present invention relates to foreign body detecting in the context of self-service terminals, such as automated teller machines (ATMs).

BACKGROUND TO THE INVENTION

ATMs are used, for example, to dispense cash and for depositing cash or cheques. An ATM usually comprises a fascia that is hingedly attached to a chassis. Typically, the fascia will include a number of slots or apertures that are aligned with modules or components of the ATM, mounted within the chassis. For instance, the fascia may include: a display aperture through which a display is visible; a slot through which a customer inserts a magnetic stripe card encoded with the customer's personal and account data; a slot through which cash is dispensed; and, a slot through which cash or cheques are deposited. The fascia also typically includes an encrypting keypad and function defined keys (FDKs) associated with the display.

Fraudsters have devised a number of schemes for stealing customers' magnetic card data or cash. One scheme, known as "skimming", involves fixing a magnetic read head to the fascia, which reads the magnetic stripe on a customer's card as it is inserted into or retrieved from the machine, and stores and/or relays the read data to a remote location. Another scheme involves fixing a cash diverting mechanism to the fascia which diverts a customer's cash as it is dispensed from or deposited into the ATM.

A foreign body is anything applied, fixed, fitted or adhered to or that settles on, engages or contacts the fascia of an ATM after it has been commissioned, that was not put there by an authorised party for a legitimate reason, although the term "body" includes not only solid objects but also liquids in whatever form (droplets, films, puddles etc.). There are two types of foreign bodies: those that are non-benign, that is, intended to defraud, cause disruption or deception, such as magnetic read heads, and those that are benign, such as rainwater.

Principally with a view to counteracting fraud, ATMs have been equipped with sensors that detect foreign bodies. One particular sensor works by determining changes in capacitance caused by a foreign body. Capacitance sensors are good for detecting foreign bodies made of metal, but poor at detecting foreign bodies made of non-metallic materials such as plastics. Fraudsters are increasingly using non-benign foreign bodies made of non-metallic materials.

SUMMARY OF THE INVENTION

Accordingly, the invention generally provides systems for and methods of providing improved detecting of foreign bodies. In particular, the invention provides an improved ability to detect non-metallic foreign bodies.

According to a first aspect there is provided a self-service terminal comprising:
 a fascia;
 a transmitter sending a chirped ultrasonic pulse across a region of the fascia;
 wherein the pulse interacts with the region and the region responds by emitting an output;
 a receiver receiving the output and producing an electrical signal corresponding to the output; and,
 an analysing module including a frequency domain analysing function transforming the electrical signal into a frequency response.

A chirped ultrasonic pulse is one whose frequency varies with time such that the pulse includes a spectrum of frequencies. Typically, the frequencies will be in the range of 30 to 100 KHz. Non-metallic as well as metallic materials interact with radiation at these frequencies.

The interaction characteristics, that is, the transmission, absorption and reflection characteristics of each region may vary with frequency, and each region may have a distinctive frequency response, whether in transmission or reflection, across the spectrum of frequencies of the pulse.

Each region of the fascia may include a part of the fascia such as a slot, the display and its associated keys or the encrypting keypad. Each part will have a frequency response to the spectrum of frequencies in the pulse. Everything else in the region will also have a frequency response. These individual frequency responses will combine to form a net frequency response of the region, which is what the frequency analysing module will indicate. The part may dominate the frequency response.

The region may also include a foreign body. Again, each foreign body will have a distinctive frequency response, and the introduction of a foreign body into the region will change the net frequency response.

Hence, the transmitter may be located such that, for example, a slot is in the region. The receiver may be placed to receive the output from the region either in transmission or reflection. Under safe working conditions, that is, without a foreign body present in the region, a baseline frequency response of the region may be established (also referred to as a control response). Then, all subsequent determinations of the frequency response can be compared to the baseline, with any divergence from the baseline indicating the presence of a foreign body in the region.

Moreover, it is possible to characterise a range of foreign bodies in terms of the effect each has on the baseline frequency response. By storing the range of characterisations and by comparing each determination of frequency response to the stored characterisations, it is possible to estimate the nature of any foreign body, when present.

A magnetic read head is likely to be placed adjacent the magnetic stripe card slot. Consequently, when attempting to detect a magnetic read head as a foreign body, the transmitter may be placed such that the region includes the magnetic stripe card slot. A cash diverting mechanism is likely to be placed adjacent the cash dispensing or depositing slot, and the transmitter may be placed accordingly. It may be that the region includes more than one slot or part of the fascia. Consequently, a foreign body placed in the region of any of the slots or parts may affect the net frequency response.

The self-service terminal (SST) may be an ATM.

The SST preferably further comprises a signal generator producing a chirped electrical pulse that the transmitter converts into a chirped ultrasonic pulse.

The transmitter is preferably located on a rear surface (that is, an inward facing surface) of the fascia so that it cannot be tampered with by someone using the SST.

The SST may further comprise a microprocessor controlling the signal generator and analysing module.

The SST may also further comprise a memory storing a baseline frequency response and/or frequency response characterisations.

Preferably, the transmitter sends a succession of pulses. In the event that the transmitter sends a succession of pulses, the baseline may be established and continually re-established as a historical average of frequency responses. Some benign foreign bodies, such as rainwater, may enter the region and gradually build up. Re-establishing the baseline as a historical average prevents such gradual build ups from being misinterpreted.

Also in the event that the transmitter sends a succession of pulses, the analysing module may also, or instead of the frequency analysing function, include a time domain analysing function. The timing of successive sent pulses may be compared with the timing of the output. For example, there may be a corresponding pulse in the output for every sent pulse, and the delay between the leading edge of a sent pulse and its corresponding output pulse may be determined. Again, a baseline may be established in the safe working condition, when the relative timing between the sent pulses and their corresponding output pulses should be substantially constant. Any change in the timing that is subsequently determined will be indicative of the presence of a foreign body. For instance, an interface, for example, of a magnetic read head, introduced into the region, may affect the timing of the output.

The transmitter and receiver may be co-located. The transmitter and receiver may be combined as a single transducer unit, in which case the SST may further comprise a switch routing electrical signals from the signal generator to the transducer and from the transducer to the frequency analysing module.

According to a second aspect, there is provided a method of detecting foreign bodies at a self-service terminal, comprising:
  sending a chirped ultrasonic pulse across a region of a fascia of the SST;
  wherein the pulse interacts with the region and the region responds by emitting an output;
  receiving the output;
  producing an electrical signal corresponding to the output; and,
  analysing the electrical signal including making a frequency domain analysis of the electrical signal involving transforming the electrical signal into a frequency response.

The method may comprise determining a baseline frequency response in the absence of foreign bodies and subsequently comparing a determined frequency response with the baseline response.

The method may comprise characterising a range of foreign bodies by determining the frequency response with each foreign body present, storing the frequency responses and comparing a determined frequency response with the stored frequency responses.

Analysing the electrical signal may additionally, or instead, include making a time domain analysis of the electrical signal.

DESCRIPTION OF EMBODIMENTS

Figure 1:
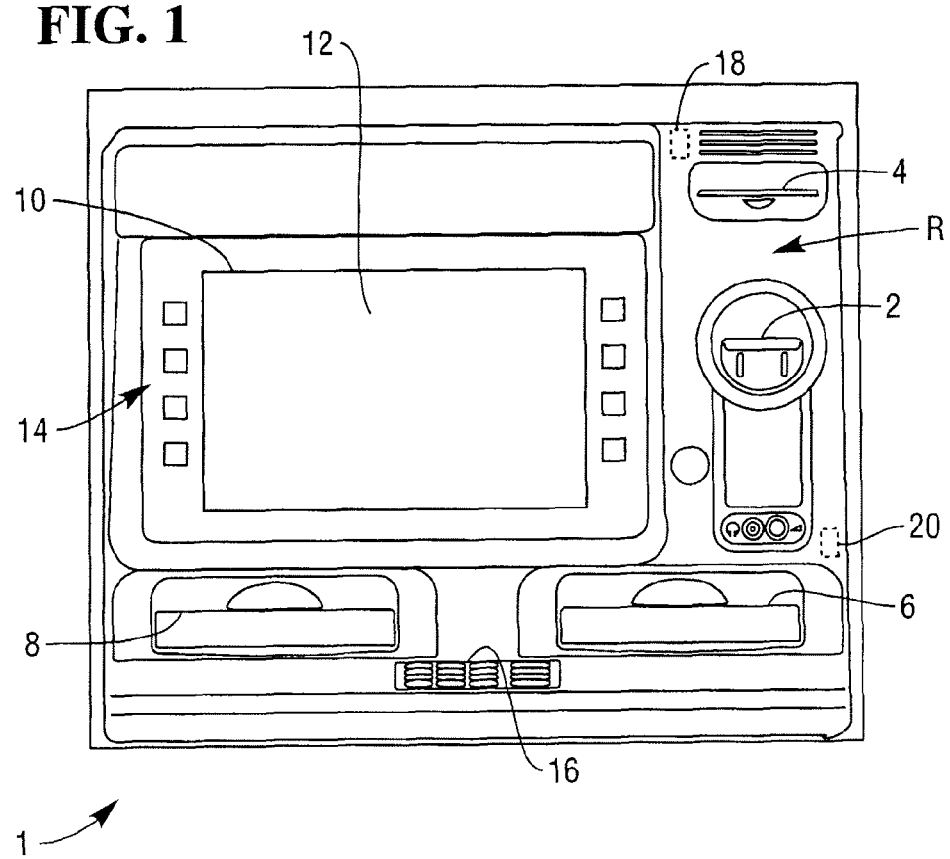
FIG. 1 is a front perspective view of part (a fascia) of an SST (an ATM) according to one embodiment of the invention.

With reference to FIG. 1, indicated generally at 1 is the fascia of an SST in the form of an ATM (not shown). It will be appreciated that the fascia 1 is illustrated in isolation. In reality, the fascia 1 would be hingedly attached to a chassis (not shown) of the ATM.

The fascia 1 has a number of parts including a display aperture 10 aligned with a display 12 mounted within the chassis. The display 12 has associated function display keys (FDKs) 14. The fascia 1 also has an encrypting keypad 16 and a number of slots, 2, 4, 6 and 8.

The first slot 2 is for a customer to insert a magnetic stripe card (not shown) into an encrypting card reader (not shown) mounted in the chassis, behind the first slot 2. The magnetic stripe card is encoded with customer personal and account data, and is used by the ATM to identify the customer.

The second slot 4 is a receipt printer slot aligned with a printer (not shown) mounted in the chassis. The printer is used to print out transaction receipts or statements, balances, etc. The third slot 6 is a currency note dispensing slot. Notes are picked from cassettes (not shown) within the chassis and delivered by a transport mechanism to the currency note slot 6 where they are presented to the customer.

The fourth slot 8 is a currency note or change depositing slot. Notes or cheques for deposit are inserted by a customer through the depositing slot 8 into a collection tray (not shown) mounted in the chassis, behind the depositing slot 8.

Figure 3:
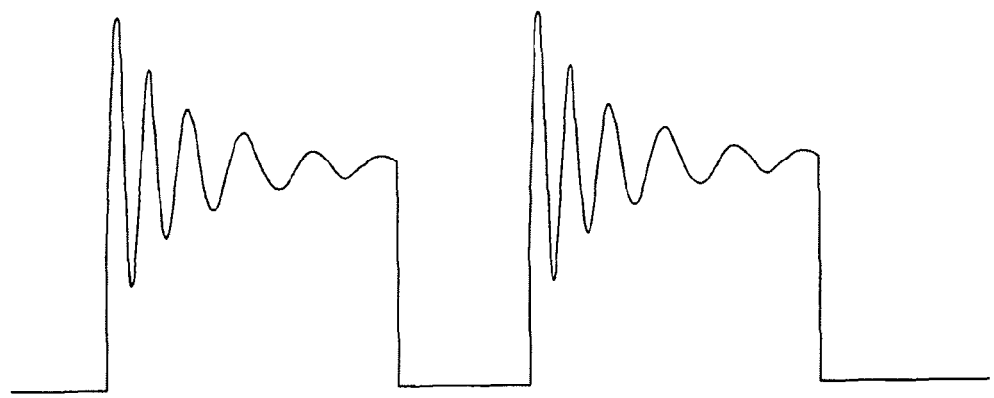

Fixed on a rear surface of the fascia 1 (that is, not the surface of the fascia that a customer can touch, but an internal surface of the fascia), adjacent the top edge of the first slot 2, is a transmitter 18 which sends a succession of ultrasonic pulses across a region R of the fascia 1. Each pulse consists of a sinusoidal wave train whose frequency varies with time between 30 and 100 KHz. In other words, the wave train includes a spectrum of frequencies. Such a pulse is known as a chirped or swept frequency pulse. FIG. 3 illustrates the swept frequency nature of the pulses, which are also damped. The transmitter 18 sends this succession of pulses through the body of the fascia 1. In other words, the transmitter 18 causes a succession of pulses to be propagated through the fascia 1.

The region R, which includes the first slot 2, the edges defining the first slot 2 and the material around the margin of the first slot 2, interacts with the pulses in the sense that each of the frequencies within the spectrum of frequencies of each pulse is transmitted, absorbed or reflected by the region R. In fact, each part of the region R, such as the first slot 2, interacts individually such that each part has its own frequency response across the spectrum of frequencies of the pulses. The individual frequency responses combine to form a net frequency response. A net transmission output of the interaction with the region R is emitted by the region R and received by a receiver 20 located adjacent the bottom edge of the first slot 2. It will be appreciated that the receiver could be co-located with the transmitter 18, in which case the received output would be the reflection output.

Figure 2:
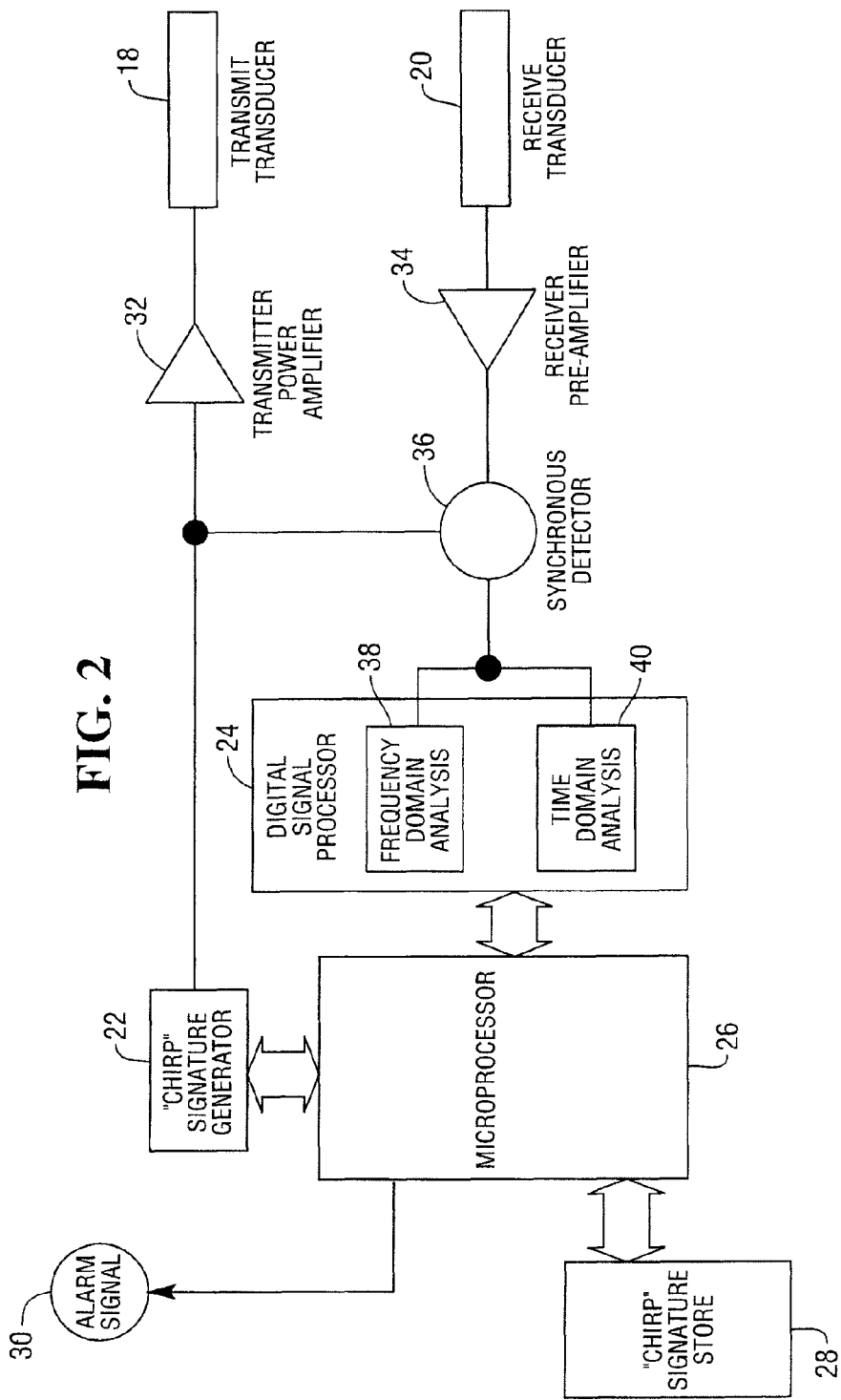
FIG. 2 is a block schematic diagram of electronic control circuitry for the fascia of FIG. 1; and,
FIG. 3 is a graphical representation of the nature of chirped ultrasonic pulses of the type applied to the fascia of FIG. 1.

With reference to FIG. 2, the transmitter 18 and receiver 20 have associated electronic control circuitry comprising a signal generator 22 and an analysing module 24. The signal generator 22 produces successive chirped electrical pulses which are fed via an amplifier 32 to the transmitter 18 where they are converted to chirped ultrasonic pulses that are sent across (that is, through) the region R of the fascia 1. In other words, the fascia 1 is the medium through which the transmitted chirped signal propagates.

The receiver 20 converts the output from the region R where it is converted to corresponding electrical signals that are fed via an amplifier 34 and a synchronous detector 36 to the analysing module 24. The analysing module 24 includes a frequency domain analysis function 38 that converts the electrical signal into a frequency response.

In the safe working state of the ATM, that is, in the absence of a foreign body in the region R (as illustrated in FIG. 1), the frequency response of the region R is established as the baseline. The baseline response is established on the basis of a historical average of the frequency responses to each of a number of pulses in the succession of pulses. The baseline response is continually re-established to allow for gradual changes in the region. For example, rainwater may gradually build up in the region and the baseline is adjusted accordingly.

The signal generator 22 and the analysing module 24 are driven by a microprocessor 26 that also has an associated memory 28. The baseline frequency response is stored in the memory 28. The output from the region R is continually received and the frequency response is continually compared to the baseline response.

If, then, a foreign body (not shown), such as a magnetic read head, is introduced into the region, by placing it adjacent the first slot 2, its individual frequency response will have an effect on the net frequency response. By adding the magnetic read head to the fascia 1, the overall characteristics of the combined fascia 1 and magnetic read head will be different to that of the fascia 1 on its own. This means that the combined magnetic read head and fascia 1 will propagate chirped pulses differently (both in time and frequency) to the fascia 1 alone. It should be appreciated that any device added to the fascia in the region will affect the propagation characteristics of the chirped signal. The pulses will interact with the read head and the read head will modify the frequencies that will be received by the receiver 20. Comparison of the net frequency response with the baseline response will reveal a divergence, which will be interpreted as the detection of a foreign body and an alarm 30 will be triggered.

What is more, it is possible to characterise the frequency responses of various different foreign bodies and to store each characteristic frequency response in the memory 28. Then, when a foreign body is detected, it is possible to estimate its nature by comparing the determined frequency response to the stored characterisations.

The analysing module 24 also includes a time domain analysis function 40. Each sent pulse has a corresponding pulse in the output. Using the synchronous detector 36, which also receives an input form the signal generator 22, the time domain analysis function 40 compares the timing of the successive sent pulses with the output. The time domain function analysis function 40 measures the delay between the leading edge of a sent pulse and the leading edge of the corresponding pulse in the output. As with the frequency response, any change in the timing is indicative of the presence of a foreign body in the region R. A baseline timing can be established by averaging over a number of historical pulses and the baseline can be continually re-established.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A self-service terminal comprising:
   a fascia;
   a transmitter sending a chirped ultrasonic pulse across a region of the fascia;
   wherein the pulse interacts with the region;
   a receiver receiving the pulse after the pulse has interacted with the region and produces an electrical output corresponding to the received pulse; and,
   an analysing module converting the electrical output to a frequency domain, the analyzing module comparing the frequesncy domain converted electrical output to a baseline frequency response.

2. A self-service terminal according to claim 1, where the frequencies of the pulse are in the range of 30 to 100 KHz.

3. A self-service terminal according to claim 1, wherein the region comprises one or more parts of the fascia.

4. A self-service terminal according to claim 1, further comprising a signal generator producing a chirped electrical pulse that the transmitter converts into a chirped ultrasonic pulse.

5. A self-service terminal according to claim 1, further comprising a microprocessor controlling the signal generator and analysing module.

6. A self-service terminal according to claim 1, further comprising a memory storing the baseline frequency response and/or frequency response characterisations.

7. A self-service terminal according to claim 1, wherein the transmitter sends a succession of pulses.

8. A self-service terminal according to claim 1, wherein the pulse is damped.

9. A self-service terminal according to claim 1, wherein the transmitter and receiver are co-located.

10. A self-service terminal according to claim 1, wherein the transmitter and receiver are combined as a single transducer unit.

11. A method of detecting foreign bodies at a self-service terminal, the method comprising:
    sending a chirped ultrasonic pulse across a region of a fascia of the terminal so that the pulse interacts with the region, wherein the region is associated with a magnetic card slot of the self- service terminal;
    receiving the pulse after the pulse has interacted with the region;
    producing an electrical output corresponding to the received pulse; and,
    analysing the electrical output by converting the electrical output to a frequency domain and comparing the frequency domain converted electrical output to a baseline frequency response.

12. A method according to claim 11, further comprising determining the baseline frequency response in the absence of foreign bodies and subsequently comparing a determined frequency response with the baseline frequency response.

13. A method according to claim 12 wherein a succession of chirped pulses are sent across the fascia and the baseline frequency response is established on the basis of a historical average of frequency responses.

14. A method according to claim 12, further comprising characterising a range of foreign bodies by determining a frequency response with each foreign body present, storing the frequency responses and subsequently comparing a determined frequency response with the stored frequency responses.

15. A method according to claim 11 wherein analysing the electrical output also, or instead of making the frequency domain analysis, includes making a time domain analysis of the electrical output.

* * * * *